United States Patent [19]

Sasaki

[11] Patent Number: 4,840,190
[45] Date of Patent: Jun. 20, 1989

[54] LOZENGE-SHAPED LOW PROFILE INJECTION RESERVOIR

[75] Inventor: Gordon H. Sasaki, Pasadena, Calif.
[73] Assignee: Dow Corning Wright, Arlington, Tenn.
[21] Appl. No.: 183,460
[22] Filed: Apr. 14, 1988

Related U.S. Application Data

[63] Continuation of Ser. No. 907,203, Sep. 12, 1986, abandoned.

[51] Int. Cl.⁴ ............................................. I61B 19/00
[52] U.S. Cl. ........................................ 128/897; 604/8; 604/93
[58] Field of Search ................... 604/8, 9, 1 R, 175, 604/93, 131, 153; 128/264, 897

[56] References Cited

U.S. PATENT DOCUMENTS

| 3,527,220 | 9/1970 | Schulte | 128/260 |
|---|---|---|---|
| 3,545,240 | 7/1971 | Mishler | 604/9 |
| 4,375,816 | 3/1983 | Labianca | 604/8 |
| 4,428,364 | 1/1984 | Bartolo | 128/1 R |
| 4,574,780 | 3/1986 | Manders | 128/1 R |
| 4,576,589 | 3/1986 | Kraus et al. | 604/8 |
| 4,588,394 | 5/1986 | Schulte et al. | 604/9 |
| 4,615,704 | 10/1986 | Frisch | 128/1 R |
| 4,634,427 | 1/1987 | Hannula et al. | 604/93 |
| 4,636,213 | 1/1987 | Pakiam | 128/1 R |
| 4,643,733 | 2/1987 | Becker | 128/1 R |
| 4,710,174 | 12/1987 | Moden et al. | 604/175 |
| 4,738,657 | 4/1988 | Hancock et al. | 604/1 R |

FOREIGN PATENT DOCUMENTS

| 8401997 | 4/1986 | Fed. Rep. of Germany | 128/1 R |
|---|---|---|---|
| 2564728 | 11/1985 | France | 128/1 R |

Primary Examiner—C. Fred Rosenbaum
Assistant Examiner—Mark F. Colosimo
Attorney, Agent, or Firm—Susan M. Cornwall

[57] ABSTRACT

Described herein is an improved injection reservoir of the type which is employed to permit subcutaneous inflation of inflatable, implantable prostheses such as tissue expanders. The improved injection reservoir has a lozenge shape when viewed from above which permits this injection reservoir to be more easily inserted and removed subcutaneously. In a more preferred embodiment, the injection reservoir has a low profile shape such that its height is no more than forth percent of its width.

1 Claim, 1 Drawing Sheet

LOZENGE-SHAPED LOW PROFILE INJECTION RESERVOIR

BACKGROUND OF THE INVENTION

This application is a continuation of application Ser. No. 907,203 filed Sept. 12, 1986 now abandoned.

This invention relates to an improved injection reservoir used for the inflation of an implantable, inflatable prosthesis such as a tissue expander.

Inflatable prostheses such as mammary prostheses and tissue expanders can be inflated subcutaneously by two commonly available means. The first means is via a resealable valve mounted directly on the surface of the prosthesis itself to permit introduction of a fluid into the prosthesis via a hypodermic syringe. Examples of such valves can be seen in U.S. Pat. Nos. 3,919,724 to Sanders, et al.; U.S. Pat. No. 4,253,201 to Ross, et al. and U.S. Pat. No. 4,428,364 to Bartolo.

The second means for inflating such a prosthesis is via an injection reservoir which is not itself expandable and has a self-sealing area designed to be punctured by a hypodermic needle to permit introduction of a fluid into the hollow center of the injection reservoir which then travels through an elongated fluid conduit such as a piece of tubing over to the inflatable prosthesis itself. Remotely placed injection reservoirs of the second type have also been referred to as "remote valves", "subcutaneous injection sites", "valve domes" and "puncture housings"; the term "injection reservoir" shall be used herein to designate such inflation means. Examples of such injection reservoirs can be seen in U.S. Pat. Nos. 3,831,583 to Edmunds, et al.; U.S. Pat. No. 3,971,376 to Wichterle; U.S. Pat. No. 4,190,040 to Schulte; U.S. Pat. No. 4,217,889 to Radovan, et al. and U.S. Pat. No. 4,543,088 to Bootman, et al. and the rectangular, oblong injection reservoir employed with the Style 20 Round/Style 22 Rectangle McGhan Tissue Expander shown in McGhan Medical Corporation (Santa Barbara, CA 93111) Product Brochure No. M005 1/85 (2 pages, 1985). The Edmunds, et al. Patent teaches a bulb-shaped injection reservoir, the Schulte, Radovan, et al. and Bootman, et al. Patents show round, dome-shaped injection reservoirs and the Wichterle Patent shows an injection reservoir with a round base and a raised, oblong capsule in the center of the base while the McGhan Tissue Expander contains a rectangular, oblong injection reservoir to "optimize palpation and filling". The Radovan, et al., Wichterle and Bootman, et al. Patents each suggest that the injection reservoir they teach may be of different sizes and shapes, but do not suggest specific shapes other than what is shown.

An implant such as a tissue expander with a remote injection reservoir may be selected because, for example, of the ease with which the injection reservoir can be found by palpation or to reduce the possibility that the prosthesis envelope itself may be accidentally damaged during inflation by a needle puncture. A subcutaneous tunnel must be created to receive the injection reservoir and round or dome-shaped injection reservoirs can turn or flip over during insertion through the tunnel if the surgeon desires to use only one incision through the skin. Dome-shaped injection reservoirs also have a relatively high profile and in places where the skin is thin such as in the face and neck region, the high profile of the dome tends to place pressure on the skin at the apex of the dome which can result in patient discomfort immediately after implantation.

The injection reservoir generally remains in place for a period of time numbering days to weeks and during that time a capsule is observed to form around the injection reservoir as well as the tubing and the inflatable portion of the tissue expander. The formation of this capsule is a natural response to the presence of the implanted prosthesis, but creates difficulties for the surgeon when the injection reservoir is to be removed if only one incision is to be used to minimize trauma and scarring. People vary in the type of capsules produced and it is sometimes difficult to remove the injection reservoir without making a second incision near the injection reservoir if a thick or tight capsule has formed. Removal difficulties are more noticeable where a rectangular or large dome-shaped injection reservoir is used.

SUMMARY OF THE INVENTION

One object of the present invention is to overcome the deficiencies of the prior art by providing an improved injection reservoir with the geometric configuration of a "lozenge" or a diamond shape which permits the injection reservoir itself to more easily be passed subcutaneously to the desired site. This shape also facilitates removal since the pointed configuration tends to push tissue aside as the injection reservoir is removed if the surgeon does not desire to make an incision throught the skin at the site of the injection reservoir. The elongated rear configuration of the injection reservoir provides a convenient tail which can be used to grip the injection reservoir during insertion and removal.

The lozenge shape coupled with the more preferred embodiment where the height of the injection reservoir is no more than forty percent of the width of the injection reservoir and the upper wall surface continuously tapers from the apex to the edge results in a low profile injection reservoir. Such a reservoir tends to distribute pressure against overlying tissue over the upper surface of the injection reservoir rather than concentrating it at the apex of a dome as does a dome-shaped injection reservoir. This results in an injection reservoir that is particularly suited for use in the face and neck regions where the skin is thin. It tends to minimize tissue necrosis due to pressure compared with higher profile injection reservoir designs and also tends to reduce a full sensation and post-operative pain in the patient as a result of the presence of the reservoir. The low profile shape still provides an adequate area for insertion of a hypodermic needle into the injection reservoir and that area can be palpated through the skin.

BRIEF DESCRIPTION OF THE DRAWINGS

The above and other objects, features, and advantages of the present invention will become apparent to those skilled in the art upon an examination of the following description and drawings which are illustrative of the present invention.

In the Drawings.

DETAILED DESCRIPTION OF THE INVENTION

Figure 1:
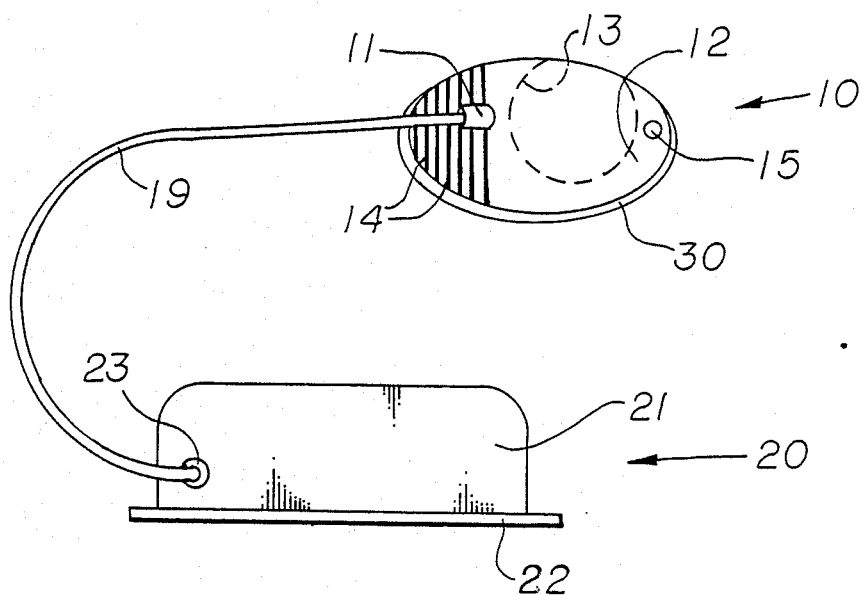
FIG. 1 is a perspective view of one embodiment of the present invention shown as injection reservoir 10.

Referring to the Drawings, FIG. 1 shows the improved injection reservoir of the present invention as injection reservoir 10 which is sealingly connected to a conventional inflatable tissue expander 20 by a fluid conduit means in the form of hollow silicone elastomer tubing 19 which is cemented within socket 11 although the tubing could be connected to injection reservoir 10 by means of other suitable means such as a hollow connector. Expander 20 is generally an inflatable silicone elastomer bag 21 which contains a base 22 and is adhered to tubing 19 by way of a silicone elastomer adhesive at 23. The actual type of inflatable prosthesis employed with the improved injection reservoir of the present invention forms no part of the present invention and that reservoir can be used with inflatable mammary prostheses, penile implants, and other such inflatable implants although a primary area of utility is in conjunction with temporarily implanted tissue expanders.

Injection reservoir 10 is composed of a body of a biocompatible, implantable material such as a medical grade silicone elastomer such as those available from Dow Corning Corporation of Midland, Mich. The exact nature of the material used forms no part of the invention as long as the material is suitable for implantation.

Referring to FIGS. 1-4, injection reservoir 10 has an upper wall 12 of a substantially non-expansible elastic material such as silicone elastomer which is sealingly attached to flat base 30 to form a hollow interior chamber 40 which communicates with the hollow center 31 of tubing 19. Puncture region 13 is located over chamber 40 and is made of a material which is self-sealing to hypodermic punctures. One such material which has been found to work well is the self-sealing silicone elastomer material described in the Bartolo U.S. Pat. No. 4,428,364 which is noted above. That material is a laminate of alternate layers of silicone elastomer and polyester mesh which has been cured and swollen with a swelling agent to create a stressed area which immediately reseals when a hypodermic needle is withdrawn. Injection reservoir 10 employs such a material and the mesh layer is indicated by reference numeral 41 in FIG. 4. Other resealable materials from which wall 12 and region 13 can be made are well known and taught in, for example, the Schulte, Radovan, et al. and Bootman, et al. Patents. To provide the preferred low profile shape shown, wall 12 continuously tapers in a relatively flat curve from its highest point or apex to the edge in a smooth fashion to thereby facilitate subcutaneous insertion of the injection reservoir.

Chamber 40 is provided with a conventional metal needlestop 42 to prevent a hypodermic needle from passing through base 30 and missing chamber 40. Needlestop 42 could be extended within base 30 beyond the area shown in the Drawings to rigidify base 30 or to permit base 30 to be more easily grasped such as where the needlestop is extended to lie beneath ridges 14. The rear portion of injection reservoir 10 contains raised ridges 14 for use in grasping the rear end of injection reservoir 10 with forceps during insertion and removal. A hole 15 passes through base 30 to permit suturing or threading of injection reservoir 10 to the subcutaneous bodily structures on which base 30 rests or to assist in insertion or extrication of injection reservoir 10 from the body by providing a site where injection reservoir 10 can be firmly fixed to an instrument or a tied to a suture.

Figure 2:
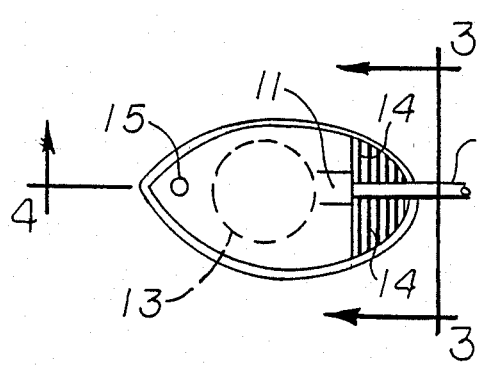
FIG. 2 is a plan view of injection reservoir 10.
Figure 3:
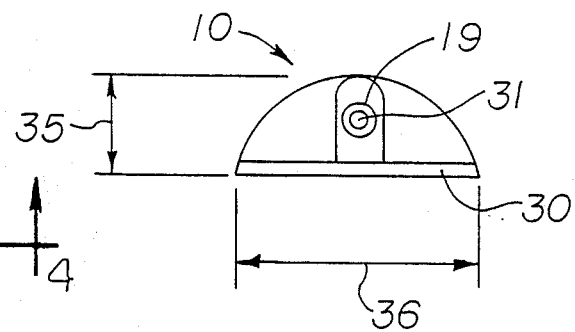
FIG. 3 is a rear view of FIG. 2 viewed from line 3—3.
Figure 4:
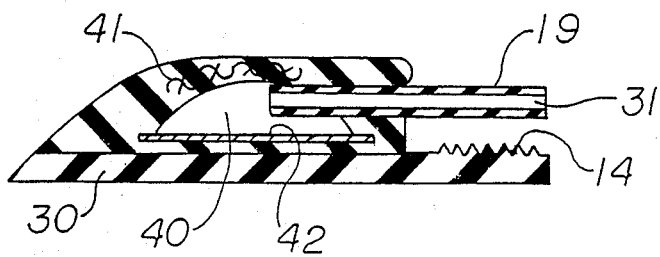
FIG. 4 is a cross-sectional view of FIG. 2 taken along section lines 4—4.

When viewed from above as shown in FIG. 2, injection reservoir 10 has a lozenge shape which is elongated and contains two acute angles at the front and rear of injection reservoir 10 and two obtuse angles forming the sides of injection reservoir 10. This general shape, which may also be in the form of an exaggerated diamond, is the improvement over prior art injection reservoir shapes provided by my invention and provides the advantages discussed above. Round, square or rectangular injection reservoirs do not possess all of the advantages that the lozenge shape provides.

The lozenge shaped injection reservoir is more preferably made in the form of a relatively low profile shape by creating an injection reservoir wherein the height shown by arrow 35 is no more than one half of the width as shown by arrow 36. Prototype injection reservoirs of the type described herein having a height of 0.375 inches (0.95 cm.), a width of 1 inch (2.54 cm.) and a length from front to rear of 1.75 inches (4.45 cm.) were found to give good results.

Other modifications of the improved injection reservoir of the present invention will become apparent to those skilled in the art from an examination of the above specification and drawings. Therefore, other variations of the present invention may be made which fall within the scope of the following Claims even though such variations were not specifically discussed above.

That which is claimed is:

1. An improved injection reservoir for subcutaneously pressurizing an inflatable implantable prosthesis of the type wherein said reservoir comprises a body of a biocompatible, implantable material having a lower base surface which is intended to be placed against bodily structures and a curved upper wall which is sealingly attached to the base surface to form a hollow interior chamber, said upper wall being of a substantially non-expansible elastic material of which at least a portion is self-sealing to penetration by a hypodermic needle to permit the hollow interior chamber to be filled by a hypodermic needle, said hollow interior chamber being sealingly connected to a fluid conduit means to permit fluid injected within said hollow interior chamber to be passed into the interior of said inflatable prosthesis, wherein the improvement comprises the body of the injection reservoir having a front end, a rear end, and two sides when viewed from above said upper wall wherein said front and rear ends are each substantially shaped as an acute angle and said sides are each substantially shaped as an obtuse angle and wherein said lower base surface being generally flat and said upper wall continuously tapers in a relatively flat curve from its highest point to its edge in a smooth fashion which facilitates insertion and removal to and from the desired site in the patient and wherein said fluid conduit means is connected to said hollow interior chamber at said rear end of the injection reservoir and said rear end has an upper surface which includes a plurality of raised ridges thereon wherein each of said ridges extends substantially parallel with the width of said injection reservoir.

* * * * *